US 6,600,040 B2

(12) United States Patent
Brands et al.

(10) Patent No.: US 6,600,040 B2
(45) Date of Patent: Jul. 29, 2003

(54) PROCESS FOR THE SYNTHESIS OF (2R, 2-ALPHA-R, 3A)-2-[1-(3,5-BIS(TRIFLUOROMETHYL)PHENYL)ETHOXY]-3-(4-FLUOROPHENYL)-1, 4-OXAZINE

(75) Inventors: Karel M. Jos Brands, Jersey City, NJ (US); Fuh-Rong Tsay, Edison, NJ (US); Karen M. Conrad, Clark, NJ (US); Matthew M. Zhao, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 25 days.

(21) Appl. No.: 09/878,042

(22) Filed: Jun. 8, 2001

(65) Prior Publication Data

US 2002/0052494 A1 May 2, 2002

Related U.S. Application Data

(60) Provisional application No. 60/210,203, filed on Jun. 8, 2000.

(51) Int. Cl.$^7$ .......................................... C07D 295/027
(52) U.S. Cl. ........................................ 544/174; 544/170
(58) Field of Search ................................ 544/174, 170

(56) References Cited

U.S. PATENT DOCUMENTS

| 5,612,337 A | 3/1997 | Baker et al. ................. 544/132 |
| 5,719,147 A | 2/1998 | Dorn et al. ............... 514/236.2 |
| 6,051,707 A | 4/2000 | Cai et al. ..................... 544/132 |
| 6,051,717 A | 4/2000 | Cai et al. ..................... 548/255 |
| 6,096,742 A | 8/2000 | Crocker et al. ............. 544/132 |
| 6,297,376 B1 | 10/2001 | Cottrell et al. .............. 544/132 |

FOREIGN PATENT DOCUMENTS

| WO | WO 95/16679 | 6/1995 |
| WO | WO 00/15621 | 3/2000 |
| WO | WO 00/26214 | 5/2000 |
| WO | WO 00/39072 | 7/2000 |

*Primary Examiner*—Venkataraman Balasubramanian
(74) *Attorney, Agent, or Firm*—J. Eric Thies; Melvin Winokur (57) ABSTRACT

The present invention is concerned with novel processes for the preparation of (2R, 2-alpha-R, 3a)-2-[1-[3,5-bis(trifluoromethyl)phenyl]ethoxy-3-(4-fluorophenyl)-1,4-oxazine. This compound is useful as an intermediate in the synthesis of compounds which possess pharmacological activity.

13 Claims, 2 Drawing Sheets

PROCESS FOR THE SYNTHESIS OF (2R, 2-ALPHA-R, 3A)-2-[1-(3,5-BIS(TRIFLUOROMETHYL)PHENYL)ETHOXY]-3-(4-FLUOROPHENYL)-1, 4-OXAZINE

CROSS REFERENCE TO RELATED APPLICATIONS

This application claims priority under 35 U.S.C. §119(e) from Provisional Application No. 60/210,203, filed Jun. 8, 2000.

BACKGROUND OF THE INVENTION

The present invention relates to processes for the preparation of (2R, 2-alpha-R, 3a)-2-[1-[3,5-bis(trifluoromethyl)phenyl]ethoxy-3-(4-fluorophenyl)-1,4-oxazine which is useful as an intermediate in the preparation of certain therapeutic agents. In particular, the present invention provides a process for the preparation of (2R, 2-alpha-R, 3a)-2-[1-[3,5-bis(trifluoromethyl)phenyl]ethoxy-3-(4-fluorophenyl)-1,4-oxazine which is an intermediate in the synthesis of pharmaceutical compounds which are substance P (neurokinin-1) receptor antagonists.

The general processes disclosed in the art for the preparation of (2R, 2-alpha-R)-4-benzyl-2-[1-[3,5-bis(trifluoromethyl)phenyl]ethoxy-1,4-oxazin-3-one result in relatively low and inconsistent yields of the desired product (see U.S. Pat. No. 5,719,147). In contrast to the previously known processes, the present invention provides more practical and economical methodology for the preparation of (2R, 2-alpha-R, 3a)-2-[1-[3,5-bis(trifluoromethyl)phenyl]-ethoxy-3-(4-fluorophenyl)-1,4-oxazine in relatively high yield and purity.

It will be appreciated that (2R, 2-alpha-R, 3a)-2-[1-[3,5-bis(trifluoro-methyl)phenyl]ethoxy-3-(4-fluorophenyl)-1,4-oxazine is an important intermediate for a particularly useful class of therapeutic agents. As such, there is a need for the development of a process for the preparation of (2R, 2-alpha-R, 3a)-2-[1-[3,5-bis(trifluoromethyl)phenyl]ethoxy-3-(4-fluorophenyl)-1,4-oxazine which is readily amenable to scale-up, uses cost-effective and readily available reagents and which is therefore capable of practical application to large scale manufacture.

Accordingly, the subject invention provides a process for the preparation of (2R, 2-alpha-R, 3a)-2-[1-[3,5-bis(trifluoromethyl)phenyl]ethoxy-3-(4-fluorophenyl)-1,4-oxazine via a very simple, short, relatively inexpensive and highly efficient synthesis.

SUMMARY OF THE INVENTION

The novel process of this invention involves the synthesis of (2R, 2-alpha-R, 3a)-2-[1-[3,5-bis(trifluoromethyl)phenyl]ethoxy-3-(4-fluorophenyl)-1,4-oxazine. In particular, the present invention is concerned with novel processes for the preparation of a compound of the formula:

This compound is an intermediate in the synthesis of compounds which possess pharmacological activity. In particular, such compounds are substance P (neurokinin-1) receptor antagonists which are useful e.g., in the treatment of psychiatric disorders, inflammatory diseases, and emesis.

DETAILED DESCRIPTION OF THE INVENTION

The present invention is directed to processes for the preparation of (2R, 2-alpha-R, 3a)-2-[1-[3,5-bis(trifluoromethyl)phenyl]ethoxy-3-(4-fluorophenyl)-1,4-oxazine of the formula:

An embodiment of the general process for the preparation of (2R, 2-alpha-R, 3a)-2-[1-[3,5-bis(trifluoromethyl)phenyl]ethoxy-3-(4-fluorophenyl)-1,4-oxazine of the formula:

comprises contacting a compound of the formula:

with a compound of the formula:

(wherein Y is selected from MgCl, MgBr, MgI and Li) in a first solvent followed by hydrogenation in a second solvent to give the compound of the formula:

In accordance with the present invention, reaction of (2R, 2-alpha-R)-4-benzyl-2-[1-[3,5-bis(trifluoromethyl)phenyl] ethoxy-1,4-oxazin-3-one with a 4-fluorophenyl organometallic reagent followed by hydrogenation provides (2R, 2-alpha-R, 3a)-2-[1-[3,5-bis(trifluoromethyl)phenyl] ethoxy-3-(4-fluorophenyl)-1,4-oxazine in high yields and in an efficient route.

Another embodiment of the present invention concerns a process for the preparation of a compound of the formula:

which comprises contacting a compound of the formula:

with a compound of the formula:

in a first solvent followed by hydrogenation in a second solvent to give the compound of the formula:

A specific embodiment of the present invention concerns a process for the preparation of (2R, 2-alpha-R, 3a)-2-[1-[3,5-bis(trifluoromethyl)phenyl]ethoxy-3-(4-fluorophenyl)-1,4-oxazine of the formula:

which is outlined as follows:

Another specific embodiment of the present invention concerns a process for the preparation of (2R, 2-alpha-R, 3a)-2-[1-[3,5-bis(trifluoromethyl)-phenyl]ethoxy-3-(4-fluorophenyl)-1,4-oxazine which is outlined as follows:

In the present invention, it is preferred that the 4-fluorophenyl organometallic reagent is selected from 4-fluorophenyl magnesium bromide, 4-fluorophenyl magnesium chloride, 4-fluorophenyl magnesium iodide and 4-fluorophenyl lithium.

The 4-fluorphenyl organometallic reagent may be prepared from the corresponding 4-fluorobromobenzene, 4-fluorochlorobenzenen or 4-fluoroiodobenzene by methods disclosed herein or known in the art.

A 4-fluorphenyl Grignard reagent may prepared from magnesium which may be in the form of magnesium granules, magnesium turnings, magnesium dust, magnesium powder, suspension of magnesium in oil, and the like. To minimize safety risks, the use of magnesium granules is preferred. Preferred solvents for preparing the 4-fluorphenyl Grignard reagent comprise an organic solvent which is selected from toluene, tetrahydrofuran (THF), diethyl ether, diglyme, and methyl t-butyl ether. For the formation of the 4-fluorphenyl Grignard reagent, tetrahydrofuran or diethyl ether are the more preferred organic solvents and tetrahydrofuran is the most preferred organic solvent. Grignard formation from 4-fluorobromobenzene under typical conditions using magnesium turnings (4 equiv.) labeled as "suitable for Grignard reactions" in diethyl ether or tetrahydrofuran and slow addition of the starting bromide results in facile formation of the Grignard reagent.

In the present invention the first solvent and the second solvent may be the same or different solvents.

In the present invention, it is preferred that the first solvent in the reaction of (2R, 2-alpha-R)-4-benzyl-2-[1-[3,5-bis(trifluoromethyl)-phenyl]ethoxy-1,4-oxazin-3-one with the 4-fluorophenyl Grignard reagent comprises a solvent which is selected from: toluene, tetrahydrofuran, 1,2-dimethoxyethane (DME), diethyl ether, diisopropyl ether, MTBE, 2-methoxyethyl ether, 1,4-dioxane, 1,3-dioxolane and mixtures thereof.

In the present invention, it is more preferred that the first solvent in the reaction of (2R, 2-alpha-R)-4-benzyl-2-[1-[3,5-bis(trifluoromethyl)phenyl]ethoxy-1,4-oxazin-3-one with the 4-fluorophenyl Grignard reagent comprises a solvent which is selected from toluene, tetrahydrofuran, and mixtures thereof. In the present invention, it is still more preferred that the first solvent in the reaction of (2R, 2-alpha-R)-4-benzyl-2-[1-[3,5-bis(trifluoromethyl)phenyl]ethoxy-1,4-oxazin-3-one with the 4-fluorophenyl Grignard reagent comprises tetrahydrofuran.

In the present invention, it is preferred that the temperature for the reaction of (2R, 2-alpha-R)-4-benzyl-2-[1-[3,5-bis(trifluoromethyl)phenyl]ethoxy-1,4-oxazin-3-one with the 4-fluorophenyl Grignard reagent is between about −70° C. to about +70° C.

In the present invention, it is more preferred that the temperature for the reaction of (2R, 2-alpha-R)-4-benzyl-2-[1-[3,5-bis(trifluoromethyl)phenyl]-ethoxy-1,4-oxazin-3-one with the 4-fluorophenyl Grignard reagent is between about 20 and 25° C.

In the present invention, it is preferred that the reaction of (2R, 2-alpha-R)-4-benzyl-2-[1-[3,5-bis(trifluoromethyl) phenyl]ethoxy-1,4-oxazin-3-one with the 4-fluorophenyl Grignard reagent is conducted with stirring.

In the present invention, it is preferred that the product resulting from the reaction of (2R, 2-alpha-R)-4-benzyl-2-[1-[3,5-bis(trifluoromethyl)phenyl]-ethoxy-1,4-oxazin-3-one with the 4-fluorophenyl Grignard reagent is contacted with an alcohol and a strong inorganic or organic acid prior to conducting the hydrogenation. The alcohol can be selected from the group of $C_1$–$C_4$ primary, secondary and tertiary alcohols, wherein methanol is the most preferred alcohol. The acid is selected from hydrochloric, hydrobromic acid, sulfuric acid, phosphoric acid, formic acid, acetic acid, trifluoroacetic acid, trichloroacetic acid, oxalic acid, tartaric acid, citric acid, malic acid, benzoic acid, 4-nitrobenzoic acid, methanesulfonic acid, trifluoromethanesulfonic acid, benzenesulfonic acid, 4-chlorobenzenesulfonic acid and 4-toluenesulfonic acid, wherein the most preferred acids are hydrochloric acid, hydrobromic acid or 4-toluenesulfonic acid.

In the present invention, it is more preferred that the product resulting from the reaction of (2R, 2-alpha-R)-4-benzyl-2-[1-[3,5-bis(trifluoromethyl)phenyl]-ethoxy-1,4-oxazin-3-one with the 4-fluorophenyl Grignard reagent iscontacted with methanol and hydrochloric acid, hydrobromic acid or 4-toluenesulfonic acid prior to conducting the hydrogenation.

In the present invention, it is more preferred that the product resulting from the reaction of (2R, 2-alpha-R)-4-benzyl-2-[1-[3,5-bis(trifluoromethyl)phenyl]-ethoxy-1,4-oxazin-3-one with the 4-fluorophenyl Grignard reagent is contacted with methanol at a temperature below about 25° C., and preferably below about 10° C., prior to conducting the hydrogenation.

In the present invention, it is preferred that the hydrogenation catalyst is a palladium catalyst, such as selected from: palladium on carbon, palladium on alumina, palladium on barium sulfate, palladium on calcium carbonate, palladium on barium carbonate, palladium on strontium carbonate, palladium on silica, and palladium hydroxide on carbon (Pearlman's catalyst).

In the present invention, it is more preferred that the hydrogenation catalyst is palladium on carbon, especially 5% or 10% palladium on carbon.

In the present invention, it is preferred that the second solvent in the hydrogenation comprises a solvent which is selected from the group of $C_1$–$C_4$ primary, secondary and tertiary alcohols, and water. Preferred solvents for the hydrogenation comprise methanol, ethanol, isopropanol, n-propanol, n-butanol, water, and mixtures thereof. More preferred solvents for the hydrogenation comprise methanol and mixtures of methanol and water.

In the present invention, it is preferred that the temperature of the reaction mixture for the hydrogenation is from about 10° C. to about 50° C., wherein the most preferred temperature is about 20–25° C.

In the present invention, it is preferred that the pressure of hydrogen during the hydrogenation is from about 1 to about 150 psi, wherein the most preferred pressure is about 5 to about 50 psi.

The present invention is further directed to salts of the compound (2R, 2-alpha-R, 3a)-2-[1-[3,5-bis(trifluoromethyl)phenyl]ethoxy-3-(4-fluorophenyl)-1,4-oxazine of the formula:

The (2R, 2-alpha-R, 3a)-2-[1-[3,5-bis(trifluoromethyl)phenyl]ethoxy-3-(4-fluorophenyl)-1,4-oxazine may be in the form of an acid addition salt, such as a salt derived from using inorganic and organic acids. Examples of such acids are hydrochloric, nitric, sulfuric, phosphoric, formic, acetic, trifluoroacetic, propionic, maleic, succinic, malonic, methanesulfonic, benzenesulfonic, para-toluene sulfonic and the like.

A preferred acid addition salt of (2R, 2-alpha-R, 3a)-2-[1-[3,5-bis(trifluoromethyl)phenyl]ethoxy-3-(4-fluorophenyl)-1,4-oxazine is the hydrochloride salt. This salt have advantages over the other known salts of (2R, 2-alpha-R, 3a)-2-[1-[3,5-bis(trifluoromethyl)phenyl]ethoxy-3-(4-fluorophenyl)-1,4-oxazine in terms of thermodynamic stability, purification and processability.

As used herein, a polymorphic form of a chemical compound is the same chemical entity, but in a different crystalline arrangement. Preferred polymorphic forms of (2R, 2-alpha-R, 3a)-2-[1-[3,5-bis(trifluoromethyl)phenyl]-ethoxy-3-(4-fluorophenyl)-1,4-oxazine hydrochloride are described herein. These polymorphic forms have advantages over the other known forms of (2R, 2-alpha-R, 3a)-2-[1-[3,5-bis(trifluoromethyl)phenyl]-ethoxy-3-(4-fluorophenyl)-1,4-oxazine hydrochloride in terms of thermodynamic stability and processability.

The (2R, 2-alpha-R, 3a)-2-[1-[3,5-bis(trifluoromethyl)phenyl]ethoxy-3-(4-fluorophenyl)-1,4-oxazine obtained in accordance with the present invention may be used as starting material in further reactions directly or following purification.

The starting materials and reagents for the subject processes are either commercially available or are known in the literature or may be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention.

EXAMPLE 1

4-Benzyl-2-hydroxy-1,4-oxazin-3-one

| Materials | MW | Density | Amount | mol | Equiv. |
|---|---|---|---|---|---|
| N-Benzylethanolamine (96%) | 151.21 | 1.065 | 7.80 kg | 49.5 (assay) | 1.0 |

-continued

| Materials | MW | Density | Amount | mol | Equiv. |
|---|---|---|---|---|---|
| Glyoxylic acid (50% in water) | 74.04 | 1.342 | 12.60 L | 114.2 | 2.31 |
| Tetrahydrofuran | 72.11 | 0.889 | 27.0 L | — | — |
| 4-Benzyl-2-hydroxy-1,4-oxazin-3-one seed | 207.23 | — | 0.252 kg | 1.24 | 0.025 |
| Water | 18.0 | 1.00 | 63.0 L | — | — |

A solution of THF (27.0 L) and 50% aqueous glyoxylic acid (12.6 L; 16.9 kg) was heated to reflux and N-benzylethanolamine (7.8 kg) was added over 45 min. The resulting mixture was refluxed for 21 h. Then the THF was distilled under atmospheric pressure while maintaining a constant volume by simultaneous addition of water (27 L). Upon completion of the distillation (<8 vol % of THF in batch) the mixture was cooled from approximately 95–100 to 79–81° C. and was optionally seeded with 4-benzyl-2-hydroxy-1,4-oxazin-3-one (250 g). Upon further cooling to room temperature the product crystallized. Crystalline 4-benzyl-2-hydroxy-1,4-oxazin-3-one was filtered, washed with water and then dried in a vacuum oven at about 60° C. under a stream of $N_2$ (72–76% yield); m.p. 134° C.

$^1$H NMR (400 MHz, CDCl$_3$) δ3.11 (ddd, J=12.5, 3.6 2.4 Hz, 1H), 3.45 (ddd, J=12.5, 10.8, 4.4 Hz, 1 H), 3.78 (ddd, J=12.1, 4.4, 2.4 Hz,1H), 4.29 (ddd, J=12.1, 10.8, 3.6 Hz, 1H), 4.51 (d, J=14.5 Hz, 1H), 4.73 (d, J=14.5 Hz, 1H), 5.40 (s, 1H), 5.76 (br s, 1H), 7.26–7.37 (m, 5H); $^{13}$C NMR (100 MHz, CDCl$_3$) δ45.6, 49.9, 57.6, 90.5, 127.9, 128.3 (2C), 128.9 (2C), 135.6, 167.3

$^1$H NMR [400 MHz, (CD$_3$)$_2$SO]δ3.10 (ddd, J=12.4, 3.8 2.0 Hz, 1H), 3.34 (ddd, J=12.4, 11.2, 4.8 Hz, 1 H), 3.68 (ddd, J=12.0, 4.8, 2.0 Hz, 1H), 4.10 (ddd, J=12.0, 11.2, 3.8 Hz, 1H), 4.46 (d, J=14.8 Hz, 1H), 4.55 (d, J=14.8 Hz, 1H), 5.06 (d, J=6.2Hz, 1H), 7.15 (d, J=6.2Hz, 1-OH), 7.23–7.36 (m, 5H); $^{13}$C NMR [100 MHz, (CD$_3$)$_2$SO]δ46.0, 49.1, 56.6, 90.6, 127.8, 128.1 (2C), 129.0 (2C), 137.2, 166.2.

EXAMPLE 2
3,5-Bis(trifluoromethyl)bromobenzene

| Materials | MW | Density | Amount | Mmol | Equiv. |
|---|---|---|---|---|---|
| 1,3-Bis(trifluoromethyl)benzene | 214.1 | 1.38 | 107 g | 500 | 1.0 |
| 96% H$_2$SO$_4$ | | | 142 mL | | |

| Materials | MW | Density | Amount | Mmol | Equiv. |
|---|---|---|---|---|---|
| Glacial HOAc | | | 22 mL | | |
| 1,3-Dibromo-5,5-dimethylhydantoin | 285.93 | | 77.25 g | 270 | 1.08 (Br$^+$) |
| 5N Aq NaOH | | | 75 mL | | |

A vigorously stirred solution of 1,3-bis(trifluoromethyl)benzene (107 g) in a mixture of glacial acetic acid (22 mL) and concentrated sulfuric acid (142 mL) was added 1,3-dibromo-5,5-dimethylhydantoin (77.25 g) at 25° C. The exothermic reaction raised the temperature to approximately 40° C. After aging at 45° C. for 4.5 h, the mixture was cooled to approximately 0° C. and poured into cold water (250 mL). After washing with 5N NaOH (75 mL) the organic layer contained 137 g of the desired 3,5-bis(trifluoromethyl)-1-bromobenzene by assay (94% yield). This product was used in the next step without further purification.

EXAMPLE 3
1-(3,5-Bis(trifluoromethyl)phenyl)ethan-1-one

| Materials | MW | Density | Amount | Mmol | Equiv |
|---|---|---|---|---|---|
| 3,5-Bis(trifluoromethyl)bromobenzene | 293.03 | 1.699 g/L | 29.3 g | 98.0 | 1.0 |

-continued

| Materials | MW | Density | Amount | Mmol | Equiv |
|---|---|---|---|---|---|
| Magnesium granules, 20 mesh | 24.3 | | 5.10 g | | 2.1 |
| Acetic Anhydride | 102.1 | 1.08 g/L | 40 mL | 423 | 4.5 |
| THF (KF = 60 μg/mL) | | | 260 mL | | |
| MTBE | | | 650 mL | | |
| Water | | | 300 mL | | |
| 50% NaOH | | | 40 mL | | |

A solution of 3,5-Bis(trifluoromethyl)bromobenzene (29.3 g) in 30 mL of THF was added to a mixture of magnesium granules (5.10 g) in THF (200 mL) heated at reflux (the reaction was initiated with approximately 5 mL of the bromide solution; the remainder was added slowly over 1 h). The mixture was aged for 30 min at reflux, cooled to RT and added over 1 h to a solution of acetic anhydride (40 mL) in THF (40 mL) maintained at −15° C. The resulting dark brown mixture was warmed to 10° C. in a water bath, and water (300 mL) was added. The pH of the vigorously stirred biphasic mixture was adjusted to 8.0 using 50% NaOH. MTBE (300 mL) was added, the layers were separated and the aqueous layer was further extracted with MTBE (3×150 mL). The organic layers were combined and concentrated in vacuo (bath at 30–35° C.; 50–80 torr). The concentrate was then distilled at atmospheric pressure to provide the pure product (20.7 g; 82% yield) with a boiling point of 187–189° C.

EXAMPLE 4
(R)-1-(3,5-Bis(trifluoromethyl)phenyl)ethan-1-ol

A solution of [Cp*RhCl$_2$]$_2$ (Cp* = pentamethylcyclopentadienyl; 6.0 g), (1S,2R)-cis-1-amino-2-indanol (3.0 g) and 1-(3,5-Bis(trifluoromethyl)phenyl)ethan-1-one (1.0 kg) in 2-propanol (7 L) was stirred for 30 min and thoroughly degassed under vacuum. Then 5 M sodium hydroxide (9 mL) was added and the mixture was aged for 3–4 h to achieve complete conversion of the starting material. The reaction mixture was poured into 1 N HCl (7 L) and extracted with heptane (2×3.5 L). The combined organic layers were washed with brine (5 L) and 1,4-diazabicyclo[2.2.2]-octane (240 g) was added. The solution was concentrated to approximately 4 mL/g of alcohol (KF<200 μg/mL; 2-propanol<5 vol %). The mixture was seeded at 40° C., allowed to cool to RT to from a seedbed and then cooled to 0° C. The crystalline product was filtered, washed with cold heptane and dried to provide the DABCO complex (70% yield; e.e.>99%).

| | | | |
|---|---|---|---|
| 1-(3,5-Bis(trifluoromethyl)-phenyl)ethan-1-one | 256.15 | 3.9 | 1 Kg |
| (Cp*RhCl$_2$)$_2$ | 618.08 | 0.01 | 6 g |
| (Cp* = Pentamethylcyclopentadienyl) | | | |
| (S,R)-cis-Aminoindanol | 149.20 | 0.02 | 3.0 g |
| NaOH | 5 N (H$_2$O) | 0.05 | 9 mL |
| IPA | | | 7 L |
| HCl | 1 N (H$_2$O) | | 7 L |
| Heptane | | | 7 L |
| 1,4-diazabicyclo[2.2.2]octane (DABCO) | 112.18 | 2.2 | 240 g |

EXAMPLE 5

(R)-1-(3,5-Bis(trifluoromethyl)phenyl)ethan-1-ol

| Materials | MW | Mol | Amt |
|---|---|---|---|
| 1-(3,5-Bis(trifluoromethyl)-phenyl)ethan-1-one | 256.15 | 11.7 | 3 Kg |
| [RuCl$_2$(p-cymene)]$_2$ (Cym = p-cymene (4-isopropyltoluene)) | 612.40 | 0.03 | 18.4 kg |
| (S,R)-cis-Aminoindanol | 149.20 | 0.06 | 9.0 g |
| NaOH | 5 N (H$_2$O) | 0.14 | 28 mL |
| IPA | | | 21 L |
| HCl | 1 N (H$_2$O) | | 21 L |
| Heptane | | | 21 L |
| 1,4-Diazabicyclo[2.2.2]octane (DABCO) | 112.18 | ~6.6 | ~740 g |

A solution of [RuCl$_2$(p-cymene)]$_2$ (18.4 g), (1S,2R)-cis-1-amino-2-indanol (9.0 g) and 1-(3,5-bis(trifluoromethyl)phenyl)ethan-1-one (3 kg) in 2-propanol (21 L) was stirred for 30 min and thoroughly degassed under vacuum. Then 5 M sodium hydroxide (28 mL) was added and the mixture was aged for 4–6 h to achieve complete conversion of the starting material. The reaction mixture was poured into 1 N HCl (21 L) and extracted with heptane (2×10.5 L). The combined organic layers were washed with brine and 1,4-diazabicyclo[2.2.2]octane (740 g) was added. The solution was concentrated to approximateky 4 ml/g of alcohol (KF<200 μg/mL; 2-propanol<5 vol %). The mixture was seeded at 40° C., allowed to cool to RT to from a seedbed and then cooled to 0° C. The crystalline product was filtered, washed with cold heptane and dried to provide the DABCO complex (75–80% yield; e.e.>99%).

EXAMPLE 6

(2R, 2-alpha-R)-4-Benzyl-2-[1-[3,5-bis(trifluoromethyl)phenyl]ethoxy-1,4-oxazin-3-one (Process 1)

| Materials | Kg | L | mol | MW | density | mol % |
|---|---|---|---|---|---|---|
| 4-Benzyl-2-hydroxy-1,4-oxazin-3-one | 2.14 | | 10.3 | 207.2 | | 100 |
| Trifluoroacetic anhydride | 2.16 | 1.46 | 10.3 | 210.0 | 1.487 | 100 |
| (R)-(3,5-bis(trifluoromethyl)phenyl)ethan-2-ol (49.5 wt % solution in acetonitrile) | 5.11 | 5.13 | 9.80 | 258.2 | 0.996 | 95 |
| Boron trifluoride etherate | 0.73 | 0.65 | 5.14 | 141.9 | 1.120 | 50 |
| 5N NaOH(aq) | 7.60 | 38.0 | | | 370 | |
| 3,7-Dimethyloctan-3-ol | 4.90 | 5.93 | 31.0 | 158.3 | 0.826 | 300 |
| Potassium t-butoxide (solid) | 0.75 | | | 112.2 | | 65 |
| Acetic acid (neat) | 0.62 | 0.59 | 10.3 | 60.05 | 1.049 | 100 |
| Acetonitrile | | 5.3 | | | | |
| Heptane | | 27 | | | | |

-continued

| Materials | Kg | L | mol | MW | density | mol % |
|---|---|---|---|---|---|---|
| 5% Sodium bicarbonate (aq) | | 5 | | | | |
| Water | | 23 | | | | |

Trifluoroacetic anhydride (2.16 kg) was added over 10 min to a dry (KF<100 μg/mL) slurry of lactam lactol (2.14 kg) in acetonitrile (5 L) cooled at 5° C. The temperature rose from 5 to 30° C. and the solids dissolved. The solution was aged for 1 h between 17–25° C. before a concentrated solution of (R)-(3,5-bis(trifluoromethyl)phenyl)ethan-2-ol in acetonitrile (5.11 kg of solution containing 2.53 kg of alcohol) was added followed by BF$_3$ etherate (0.65 L). The temperature rose from 17 to 27° C. and the mixture was aged for 4 h before 5 M NaOH (7.6 L) was added slowly while maintaining the temperature below 27° C. followed by 3,7-dimethyloctan-3-ol (5.9 L). The resulting mixture was distilled at atmospheric pressure until the vapor temperature reached 92° C. and most of the acetonitrile was distilled off. Water (5 L) and heptane (8 L) were added and the mixture was warmed to 45° C. The organic layer was separated, washed with water (13 L) at 45–50° C. and then diluted with heptane (16 L). The solution was dried via an azeotropic distillation until KF<130 μg/mL (6 L of distillate collected; 3 L of fresh heptane added). The solution was cooled to RT and seeded with the (R,R) diastereomer (50 mg). Upon formation of a seedbed the slurry was cooled to −10° C. and potassium tert-butoxide (752 g) was added in one portion. The mixture was aged between −12 and −7° C. for 8.5 h when virtually all of the undesired diastereomer had been converted to the desired (R,R) diastereomer according to HPLC analysis. Acetic acid (0.59 L) was added followed by a 5% NaHCO$_3$ in water solution (5 L). The biphasic mixture was warmned to 45–50° C. The organic layer was separated, washed with water (5 L) at 45–50° C. and concentrated via distillation at atmospheric pressure to a total volume of 24 L (12 L of distillate collected). Upon cooling to 35° C. a seedbed formed. The slurry was cooled to −10° C. and then filtered. The solids were washed with cold heptane (4.5 L) and dried in vacuo to provide the pure product (3.66 kg; 83% overall yield).

EXAMPLE 7
(2R, 2-alpha-R)-4-Benzyl-2-[1-[3,5-bis(trifluoromethyl)phenyl]ethoxy-1,4-oxazin-3-one (Process 2)

| Materials | Kg | L | mol | MW | density | mol % |
|---|---|---|---|---|---|---|
| 4-Benzyl-2-hydroxy-1,4-oxazin-3-one | 2.03 | | 9.80 | 207.2 | | 100 |
| Trifluoroacetic anhydride | 2.06 | 1.38 | 10.3 | 210.0 | 1.487 | 100 |
| (R)-(3,5-bis(trifluoromethyl)phenyl)ethan-2-ol (49.5 wt % solution in acetonitrile) | 4.85 | 4.87 | 9.30 | 258.2 | 0.996 | 95 |
| Boron trifluoride etherate | 0.69 | 0.62 | 4.86 | 141.9 | 1.120 | 50 |
| 5N NaOH(aq) | | 8.1 | 40.5 | | | 410 |
| 3,7-Dimethyloctan-3-ol | | 1.68 | 2.03 | 10.6 | 158.3 | 0.826 |
| Potassium 3,7-dimethyloct-3-oxide (48.7 wt % in heptane, 1.99M) | 1.09 | 1.36 | 2.70 | 196.4 | 0.803 | 28 |
| Acetic acid (neat) | 0.28 | 0.29 | 4.66 | 60.05 | 1.049 | 47 |
| Acetonitrile | | 4.8 | | | | |
| Heptane | | 21 | | | | |
| 5% Sodium bicarbonate (aq) | | 4.1 | | | | |
| Water | | 20.4 | | | | |

Trifluoroacetic anhydride (2.056 kg) was added over 10 min to a dry (KF<140 μg/mL) slurry of lactam lactol (2.03 kg) in acetonitrile (4.8 L) cooled at 5° C. The temperature rose from 5 to 34° C. and the solids dissolved. The solution was aged for 1 h between 17–25° C. before a concentrated solution of (R)-(3,5-bis(trifluoromethyl)phenyl)ethan-2-ol in acetonitrile (4.85 kg of solution containing 2.40 kg of alcohol) was added followed by BF$_3$ etherate (0.62 L). The temperature rose from 17 to 28° C. and the mixture was aged for 2 h before 5 M NaOH (8.1 L) was added slowly while maintaining the temperature below 27° C., followed by 3,7-dimethyloctan-3-ol (2.0 L). The resulting mixture was distilled at atmospheric pressure until the vapor temperature reached 92° C. and most of the acetonitrile was distilled off (8.1 L of distillate collected). Water (4.1 L) and heptane (12.2 L) were added and the mixture was warmed to 45° C. The organic layer was separated, washed with water (12.2 L) at 45–50° C. and then diluted with heptane (6 L). The solution was dried via an azeotropic distillation until KF<130 μg/mL (7.8 L of distillate collected). The solution was cooled to RT and seeded with the (R,R) diastereomer (50 mg). Upon formation of a seedbed the slurry was cooled to −11° C. and potassium 3,7-dimethyloct-3-oxide (1.09 kg; 48.7 wt % solution in heptane) was over 10 min. The mixture was aged between −12 and −7° C. for 5 h during which virtually all of the undesired diastereomer had been converted to the desired (R,R) diastereomer according to HPLC analysis. Acetic acid (0.28 L) was added followed by a 5% NaHCO$_3$ in water solution (4.1 L). The biphasic mixture was warmed to 45–50° C. The organic layer was separated, washed with water (4.1 L) at 45–50° C. and concentrated via distillation at atmospheric pressure to a total volume of 16 L (4.1 L of distillate collected). The solution was seeded at 45° C. and then allowed to cool to RT. The slurry was cooled to 5° C., aged for 1.5 h and then filtered. The solids were washed with cold heptane (3.0 L) and dried in vacuo to provide the pure product (3.51 kg; 84% overall yield).

EXAMPLE 8

(2R, 2-alpha-R, 3a)-2-[1-[3,5-bis(trifluoromethyl)phenyl]ethoxy-3-(4-fluorophenyl)-1,4-oxazine (Process 1)

A solution of (2R, 2-alpha-R)-4-benzyl-2-[1-[3,5-bis(trifluoromethyl)-phenyl]ethoxy-1,4-oxazin-3-one (4.80 g) in toluene (27 mL) was cooled to −6° C. and a solution of 4-fluorophenylmagnesium bromide in THF (27 mL; 0.93 M) was added slowly such that T<0° C. The resulting clear solution was aged for 1 h and then quenched into aqueous citric acid (10 wt %; 27 mL). Toluene (27 mL) was added and the organic layer was separated and washed with 0.5 M sodium bicarbonate solution and water (25 mL each). The solution was partially concentrated to a total volume of approximately 20 mL and then diluted with methanol to a total volume of 90 mL. 4-Toluenesulfonic acid monohydrate (1.95 g) and 10% Pd/C catalyst (950 mg) were added and the mixture was hydrogenated under 5 psi of hydrogen at RT for 4 h. The catalyst was filtered and washed with additional methanol (90 mL). The combined filtrates were concentrated to dryness. The residue was dissolved in 60 mL of hot toluene. Upon slow cooling crystals were formed. After cooling to RT, heptane (60 mL) was added. After filtration and drying, (2R, 2-alpha-R, 3a)-2-[1-[3,5-bis(trifluoromethyl)phenyl]ethoxy-3-(4-fluorophenyl)-1,4-oxazine as the tosylate salt was obtained in 89% overall yield.

EXAMPLE 9

(2R, 2-alpha-R, 3a)-2-[1-[3,5-bis(trifluoromethyl)phenyl]ethoxy-3-(4-fluorophenyl)-1,4-oxazine (Process 2)

A solution of 4-fluorophenylmagnesium bromide in THF (150 mL; 0.93 M) was slowly added to a solution of (2R, 2-alpha-R)-4-benzyl-2-[1-[3,5-bis(trifluoromethyl)phenyl]ethoxy-1,4-oxazin-3-one (49.5 g) in THF (50 mL) between 20 and 25° C. The resulting clear solution was aged for 30 min and then added slowly into cold methanol (100 mL) such that T<20° C. A solution of 4-toluenesulfonic acid monohydrate (42.1 g) in methanol (50 mL) was added to the slurry followed by the 5% Pd/C catalyst (16.5 g; 55 wt % wet). The resulting mixture was hydrogenated under 5 psi of hydrogen at RT for 3 h. The catalyst was filtered and washed with methanol (100 mL). The combined filtrates were concentrated via distillation at atmospheric pressure to a total volume of approximately 350 mL. The distillation was continued while keeping the volume constant at 350 mL via slow addition of 4-methyl-2-pentanone (methyl-isobutyl ketone; MIBK; 450 mL). Upon completion of the distillation, the resulting slurry was allowed to cool to 20–30° C. and washed with 500 mL of a solution of trisodium citrate dihydrate (10 wt %) and sodium bicarbonate (1.0 M) in water. Concentrated hydrochloric acid (11.9 g; 37.3 wt %) was added to the organic layer and the clear solution was concentrated under atmospheric pressure to a total volume of approximately 180 mL. The resulting product slurry was cooled from 118° C. to 5° C. and filtered. The solids were washed with methyl-isobutyl ketone (MIBK) and dried in vacuo at 40° C. to afford 46.4 g of (2R, 2-alpha-R, 3a)-2-[1-[3,5-bis(trifluoro-methyl)phenyl]ethoxy-3-(4-fluorophenyl)-1,4-oxazine as the hydrochloride salt in 87% overall yield.

Figure 1:
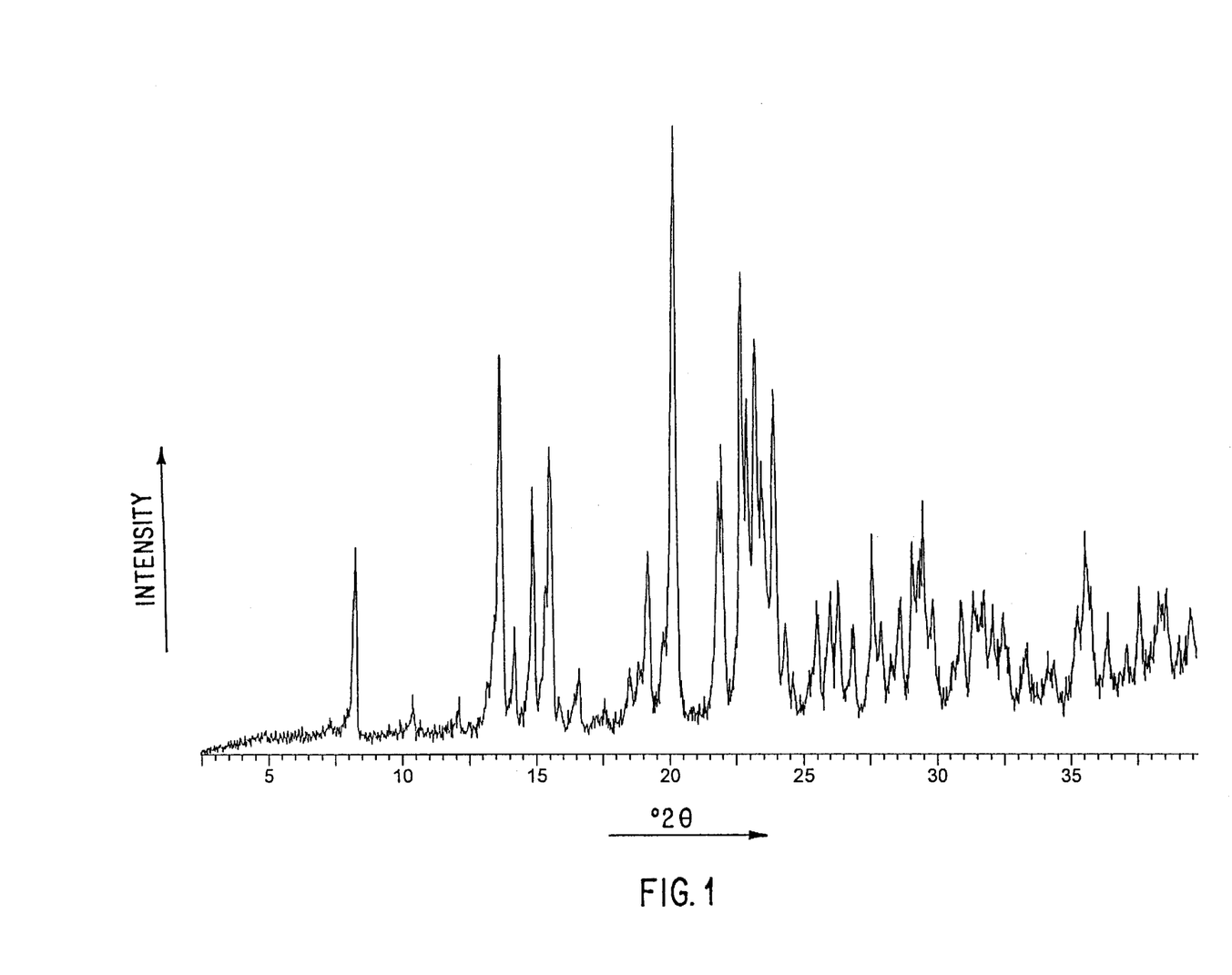
FIG. 1 is an X-ray powder diffraction pattern of Form I of (2R, 2-alpha-R, 3a)-2-[1-[3,5-bis(trifluoromethyl)phenyl]ethoxy-3-(4-fluorophenyl)-1,4-oxazine hydrochloride.
Figure 2:
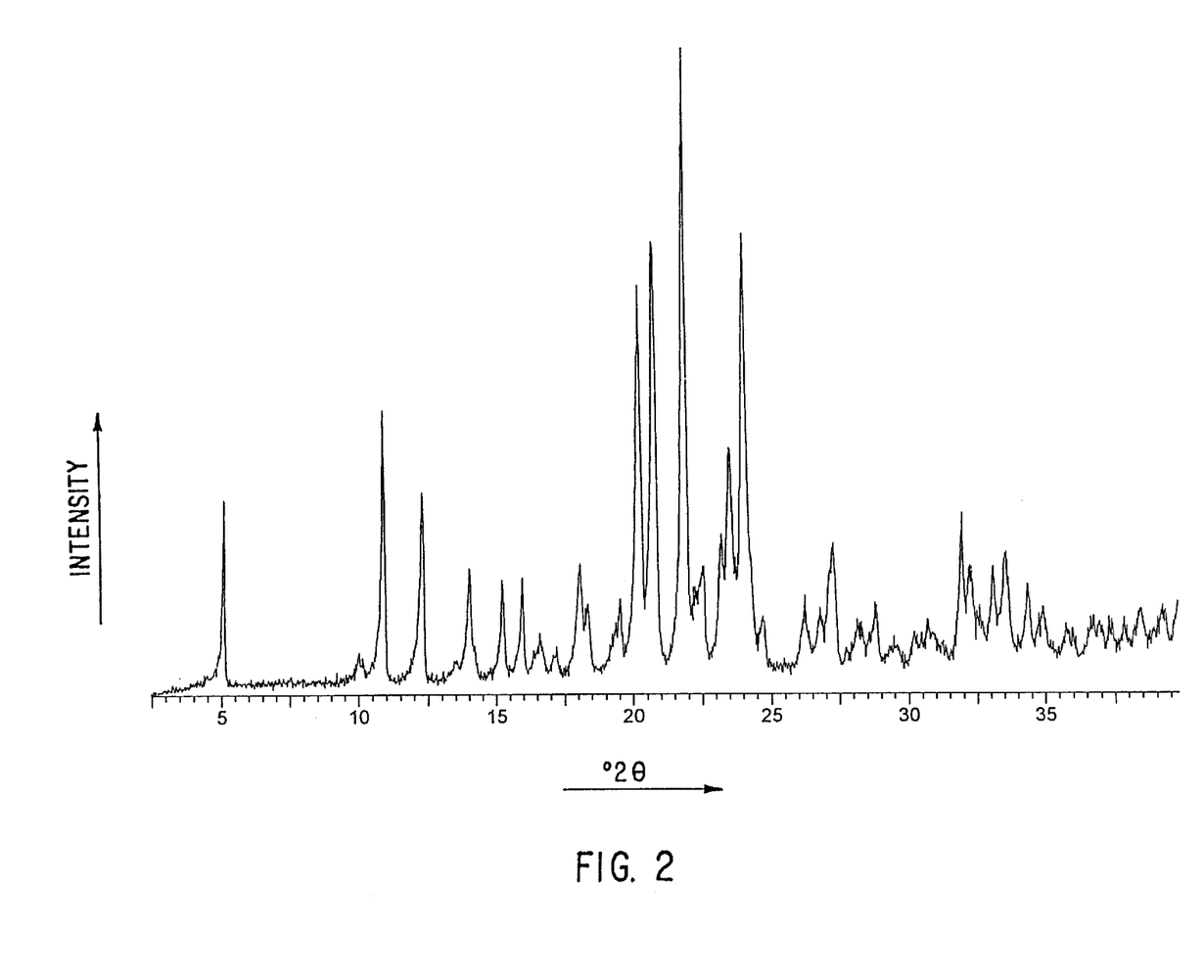
FIG. 2 is an X-ray powder diffraction pattern of Form II of (2R, 2-alpha-R, 3a)-2-[1-[3,5-bis(trifluoromethyl)phenyl]ethoxy-3-(4-fluorophenyl)-1,4-oxazine hydrochloride.

Two polymorphic forms of (2R, 2-alpha-R, 3a)-2-[1-[3,5-bis(trifluoro-methyl)phenyl]ethoxy-3-(4-fluorophenyl)-1,4-oxazine hydrochloride (Form I and II) are chracterized below by virtue of their X-Ray Powder Diffraction (XRPD) patterns. The XRPD patterns were collected on a Philips PW 3710 MPD control automated power diffractometer. The x-ray generator employed a copper target, an accelerating potential of 45 kV and a filament emission of 40 mA. Diffraction patterns were collected from 2 to 40 degrees.

Form I of (2R, 2-alpha-R, 3a)-2-[1-[3,5-bis(trifluoromethyl)-phenyl]ethoxy-3-(4-fluorophenyl)-1,4-oxazine hydrochloride was characterized by an X-ray powder diffraction pattern with key reflections at approximately: 13.71, 20.23, 22.70 and 23.26° (2 theta).

Additional XRPD data pertaining to this polymorphic form (Form I) is presented below in Table 1 (Generator settings: 45 kV, 40 mA; Cu alpha1, 2 wave lengths 1.54060, 1.54439 Ang) and in FIG. 1.

TABLE 1

| Peak No. | D Spacing (Ang) | I/Imax (%) |
|---|---|---|
| 1 | 10.68 | 31.7 |
| 2 | 6.45 | 65.5 |
| 3 | 5.94 | 42.8 |
| 4 | 5.78 | 25.1 |
| 5 | 5.70 | 44.6 |
| 6 | 4.61 | 27.0 |
| 7 | 4.38 | 100.0 |
| 8 | 4.06 | 43.4 |
| 9 | 4.04 | 50.5 |
| 10 | 3.91 | 73.8 |
| 11 | 3.88 | 57.8 |
| 12 | 3.82 | 66.1 |
| 13 | 3.79 | 45.2 |
| 14 | 3.73 | 48.5 |
| 15 | 3.71 | 56.8 |
| 16 | 3.42 | 23.0 |
| 17 | 3.38 | 24.2 |
| 18 | 3.23 | 34.7 |
| 19 | 3.11 | 21.3 |
| 20 | 3.07 | 33.2 |
| 21 | 3.03 | 40.4 |
| 22 | 2.99 | 22.1 |
| 23 | 2.89 | 22.3 |
| 24 | 2.85 | 21.9 |
| 25 | 2.82 | 23.8 |
| 26 | 2.79 | 21.5 |
| 27 | 2.76 | 20.5 |
| 28 | 2.52 | 34.9 |
| 29 | 2.51 | 25.6 |
| 30 | 2.39 | 23.9 |
| 31 | 2.35 | 23.0 |
| 32 | 2.33 | 23.2 |

Form II of (2R, 2-alpha-R, 3a)-2-[1-[3,5-bis(trifluoromethyl)-phenyl]ethoxy-3-(4-fluorophenyl)-1,4-oxazine hydrochloride was characterized by an X-ray powder diffraction pattern with key reflections at approximately: 20.24, 20.79, 21.88 and 24.03° (2 theta).

Additional XRPD data pertaining to this polymorphic form (Form II) is presented below (Generator settings: 45 kV, 40 mA; Cu alpha1, 2 wave lengths 1.54060, 1.54439 Ang) and in FIG. 2.

TABLE 2

| Peak No. | D Spacing (Ang) | I/Imax (%) |
|---|---|---|
| 1 | 17.32 | 31.5 |
| 2 | 8.10 | 43.3 |
| 3 | 7.19 | 30.3 |
| 4 | 6.32 | 18.0 |

TABLE 2-continued

| Peak No. | D Spacing (Ang) | I/Imax (%) |
|---|---|---|
| 5 | 5.55 | 17.0 |
| 6 | 4.92 | 18.1 |
| 7 | 4.38 | 64.1 |
| 8 | 4.27 | 67.6 |
| 9 | 4.06 | 100.0 |
| 10 | 3.94 | 16.9 |
| 11 | 3.84 | 23.9 |
| 12 | 3.78 | 37.8 |
| 13 | 3.70 | 73.4 |
| 14 | 3.27 | 19.9 |
| 15 | 2.80 | 22.6 |
| 16 | 2.78 | 16.9 |
| 17 | 2.71 | 18.6 |
| 18 | 2.67 | 19.7 |
| 19 | 2.61 | 15.7 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the formula:

which comprises contacting a compound of the formula:

with a compound of the formula:

wherein Y is selected from MgCl, MgBr, MgI and Li, in a first solvent followed by hydrogenation in a second solvent to give the compound of the formula:

2. The process of claim 1 wherein Y is MgBr.

3. The process of claim 1 wherein the first solvent comprises a solvent which is selected from: toluene, tetrahydrofuran, 1,2-dimethoxyethane (DME), diethyl ether, diisopropyl ether, MTBE, 2-methoxyethyl ether, 1,4-dioxane, 1,3-dioxolane and mixtures thereof.

4. The process of claim 1 wherein the first solvent comprises a solvent which is selected from: toluene, tetrahydrofuran, and mixtures thereof.

5. The process of claim 1 wherein the first solvent comprises tetrahydrofuran.

6. The process of claim 1 wherein the product resulting from the reaction of (2R, 2-alpha-R)-4-benzyl-2-[1-[3,5-bis(trifluoromethyl)phenyl]-ethoxy-1,4-oxazin-3-one with the 4-fluorophenyl reagent is contacted with an alcohol and a strong inorganic or organic acid prior to conducting the hydrogenation.

7. The process of claim 1 wherein the product resulting from the reaction of (2R, 2-alpha-R)-4-benzyl-2-[1-[3,5-bis(trifluoromethyl)phenyl]-ethoxy-1,4-oxazin-3-one with the 4-fluorophenyl Grignard reagent is contacted with methanol and hydrochloric acid, hydrobromic acid or 4-toluenesulfonic acid prior to conducting the hydrogenation.

8. The process of claim 1 wherein the hydrogenation is catalytic hydrogenation.

9. The process of claim 8 wherein the hydrogenation catalyst is selected from: palladium on carbon, palladium on alumina, palladium on barium sulfate, palladium on calcium carbonate, palladium on barium carbonate, palladium on strontium carbonate, palladium on silica, and palladium hydroxide on carbon.

10. The process of claim 9 wherein the hydrogenation catalyst is palladium on carbon.

11. The process of claim 1 wherein the second solvent comprises a solvent which is selected from the group of $C_1$–$C_4$ primary, secondary and tertiary alcohols, and water.

12. The process of claim 1 wherein the second solvent comprises a solvent which is selected from methanol, ethanol, isopropanol, n-propanol, n-butanol, water, and mixtures thereof.

13. The process of claim 1 wherein the second solvent comprises a solvent which is selected from methanol and mixtures of methanol and water.

* * * * *